(12) United States Patent
Kulikowski et al.

(10) Patent No.: US 8,173,610 B2
(45) Date of Patent: May 8, 2012

(54) DERIVATIVES OF EPIRUBICIN, THEIR MEDICINAL APPLICATION AND PHARMACEUTICALY ACCEPTABLE FORMS OF DRUGS

(75) Inventors: Tadeusz Kulikowski, Warsaw (PL); Maria Bretner, Wolomin (PL); Andzelika Najda, Lubartow (PL); Lucyna Cova, Lyons (FR); Christian Trepo, Bron (FR); Ramamurthy Narayan, Headington (GB); Andrzej Piasek, Warsaw (PL); Andrzej Lipniacki, Warsaw (PL); Wlodzimierz Zagorski-Ostoja, Warsaw (PL)

(73) Assignees: Instytut Biochemii I Biofizyki, Warsaw (PL); Institut National de Las Sante Et de la Recherche Medicale (Inserm), Paris (FR); Instytut Medycyny Doswiadczalnej I Kliniczne, Warsaw (PL)

( * ) Notice: Subject to any disclaimer, the term of this patent is extended or adjusted under 35 U.S.C. 154(b) by 495 days.

(21) Appl. No.: 12/159,477

(22) PCT Filed: Nov. 14, 2006

(86) PCT No.: PCT/PL2006/000080
§ 371 (c)(1),
(2), (4) Date: Nov. 21, 2008

(87) PCT Pub. No.: WO2007/075094
PCT Pub. Date: Jul. 5, 2007

(65) Prior Publication Data
US 2009/0247623 A1 Oct. 1, 2009

(30) Foreign Application Priority Data

Dec. 27, 2005 (PL) .......................................... 378535
Dec. 29, 2005 (WO) ................. PCT/PL2005/000086

(51) Int. Cl.
*C08B 3/00* (2006.01)
*C08B 5/00* (2006.01)

(52) U.S. Cl. ................ 514/34; 514/25; 514/33; 536/4.1

(58) Field of Classification Search .................... None
See application file for complete search history.

(56) References Cited

FOREIGN PATENT DOCUMENTS

| DE | 2757102 A1 | 7/1978 |
| DE | 3500029 A1 | 9/1986 |
| EP | 0299527 | * 4/1992 |
| EP | 1721614 A1 | 11/2006 |

OTHER PUBLICATIONS

Cotterill et al. Organic Process Research & Development (2005), vol. 9, pp. 818-821.*
Bodley et al. Cancer Research (1989), vol. 49, pp. 5969-5978.*
Borowski et al. "Nucleotide Triphosphatase/Helicase of Hepatitis C Virus as a Target for Antiviral Therapy", Antiviral Research 2002. vol. 55, p. 397-412.
Ul'Yanova et al. "Synthesis and Antitumor Properties of 3'-Desamino-3'-Dimethylformamidino-Doxorubicin", Antibiotiki I Khimioterapiya 1989, vol. 34, No. 2, p. 105-109.
Launchbury et al. "Controversy: Epirubicin and Doxorubicin: A Comparison of Their Characteristics, Therapeutic Activity and Toxicity", Cancer Treatment Reviews 1993, vol. 19, p. 197-228.
Laskus et al. "Hepatitis C Virus in Lymphoid Cells of Patients Coinfected with Human Immunodeficiency Virus Type 1: Evidence of Active Replication in Monocytes/ Mactophages and Lymphocytes", Journal of Infectious Diseases 2000, vol. 181, p. 442-448.
Guo et al. "Effect of Alpha Interferon on the Hepatitis C Virus Replicon", Journal of Virology Sep. 2001, vol. 75, No. 18, p. 8516-8523.
Vrolijk et al. "A Replicon-Based Bioassay for the Measurement of Interferons in Patients with Chronic Hepatitis C", Journal of Virological Methods 2003, vol. 110, p. 201-209.
Rice et al. "The Hepatitis C Viruses" vol. 242 of Current Topics in Microbiology and Immunology, Springer 2000, 381 Pages, Section from Book: "Cronic Infection" D. Theodore and M.W. Fried, p. 45-46, Natural History and Disease Manifestations of Hepatitis C Infection.

* cited by examiner

*Primary Examiner* — Patrick Lewis
(74) *Attorney, Agent, or Firm* — Brooks Kushman P.C.

(57) ABSTRACT

The present invention relates to novel derivatives of epirubicin, pharmaceutical composition comprising these derivatives, and uses of epirubicin and its derivative for treating HCV.

21 Claims, 5 Drawing Sheets

Figure 1:
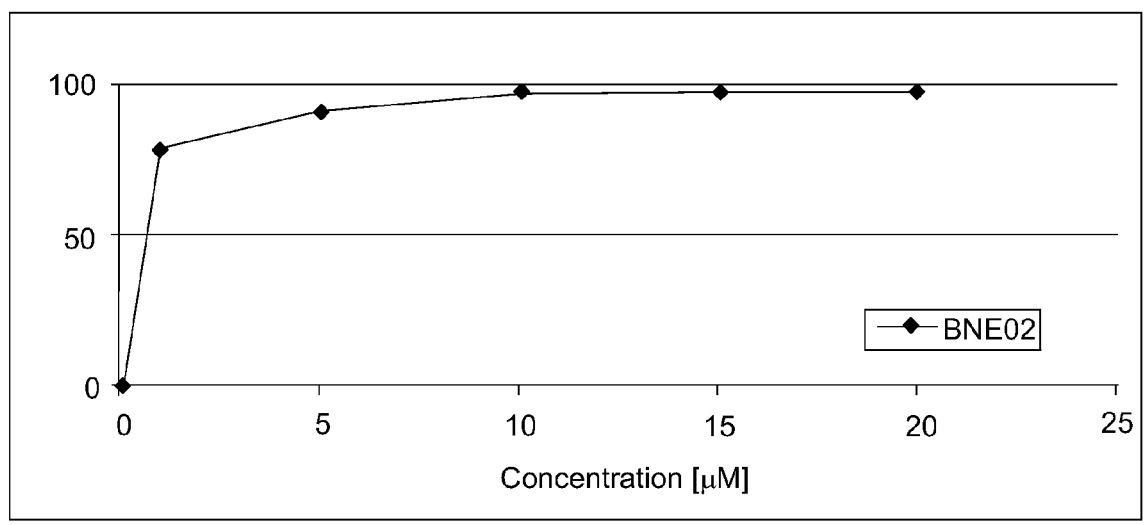

DERIVATIVES OF EPIRUBICIN, THEIR MEDICINAL APPLICATION AND PHARMACEUTICALY ACCEPTABLE FORMS OF DRUGS

The present invention relates to novel derivatives of epirubicin, pharmaceutical compositions comprising these derivatives, and uses of epirubicin and its derivative for treating HCV.

HCV is of particular importance: it is highly pathogenic member of hepaciviruses of Flaviviridae superfamily, widely distributed overall the world (according to WHO report ca 300 millions infected people). Chronic active hepatitis C develops in over 85% of acutely infected carriers and leads to liver cirrhosis and hepatocellular carcinoma (Hagedorn and Rice, Eds., The Hepatitis C Viruses, Springer, Heidelberg 2000).

Since the discovery of HCV, numerous trials have been made for anti-HCV chemotherapeutic agents. However, only combination of nucleoside ribavirin with interferon α2b or α2a and/or its pegylated derivatives were approved for the treatment of HCV infections. In addition these therapies are only partially effective (40-50% "cures") and cause a lot of undesired side effects such as: influenza-like symptoms, headache, hemolysis, nausea, anorexia, anemia, etc. Therefore there is a great need for other anti-HCV agents or methods suitable to control the chronic infection and to reduce progression to liver cirrhosis and hepatocellular carcinoma.

At present, the inventors surprisingly discovered that epirubicin derivatives presented in Formula 1, as referred to below, exert potent inhibitory activity against HCV replication. The invention shows that this activity is observed at doses below the cytotoxicity of epirubicin in Huh7, PBMC or Vero cells. The invention further shows that these derivatives have better in vitro therapeutic index (TI) (Table 1), and lower in vivo toxicity in mice. In addition, the inventors surprisingly discovered that epirubicin and its derivatives are effective for treating HCV infection at a very low doses, particularly at a dose associated with low or less toxicity.

By epirubicin is intended 7-O-(3'-amino-2',3',6'-trideoxy-α,β-L-arabinohexopyranosyl)-adriamycinone (epirubicin, 4'epidoxyrubicin).

A particular object of this invention thus resides in compounds represented by Formula 1:

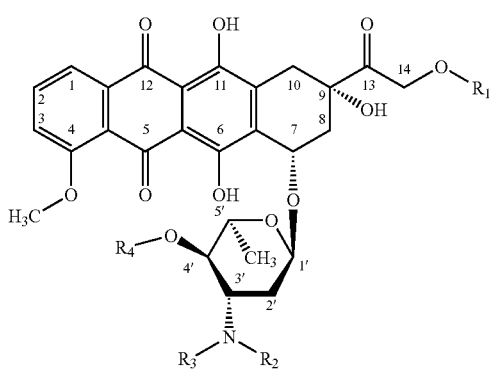

Formula 1 wherein $R_1$, $R_2$, $R_3$, and $R_4$ are the same or different and represent a hydrogen atom; a linear or branched alkyl group comprising from 1 to 5 carbon atoms (such as methyl, ethyl, propyl and isopropyl); a linear or branched alkenyl or alkynyl group with an alkyl chain containing 1 to 5 carbon atoms; an alkyl carbonyl group containing 1 to 5 carbon atoms (such as an acetyl group); or a formamidinyl or dialkylformamidinyl group (with an alkyl chain containing 1 to 5 carbon atoms), preferably with the provision that at least one of $R_1$, $R_2$, $R_3$, and $R_4$ is not hydrogen; and any pharmaceutically acceptable salts thereof.

In a preferred embodiment, at least one of $R_1$, $R_2$, $R_3$, and $R_4$ is an hydrogen atom.

In a further preferred embodiment, at least one of $R_1$, $R_2$, $R_3$, and $R_4$ is an alkyl carbonyl group, more preferably an acetyl group.

In a particular embodiment, $R_3$ is an acetyl group.

In a further preferred embodiment, at least one of $R_1$, $R_2$, $R_3$, and $R_4$ is an alkyl group, particularly a methyl group.

In an other preferred embodiment, at least one of $R_1$, $R_2$, $R_3$, and $R_4$ is a dialkylformamidinyl group, preferably a dimethylformamidinyl group.

According to particular embodiments, the invention concerns a compound of Formula 1, wherein:

$R_1$, $R_2$, and $R_4$ are hydrogen and $R_3$ is acetyl, or $R_2$ is hydrogen and $R_1$, $R_3$ and $R_4$ are acetyl, or $R_1$, $R_2$, and $R_4$ are hydrogen and $R_3$ is dimethylformamidinyl or formamidinyl, or $R_1$ and $R_4$ are hydrogen and $R_2$ and $R_3$ are methyl groups, or, $R_1$ and $R_2$ represent an hydrogen atom and $R_3$ and $R_4$ represent acetyl groups, and pharmaceutically acceptable salts thereof.

Compounds of this invention may be prepared following chemical methods known per se in the art, using epirubicin as a starting material, as illustrated in the examples.

The present invention also concerns a pharmaceutical composition comprising at least one compound as defined above and a pharmaceutically acceptable carrier. The carrier may be any solvent, saline solution, powder, stabilizer, tension-active, etc., that is used in the pharmaceutical industry.

The compounds may be in the form of any pharmaceutically acceptable salt, such as acid or basic addition salts, hydrochloride.

The present invention also relates to a compound as defined above or a salt thereof, as a medicament, particularly for treating or preventing an HCV infection in a mammalian subject, particularly a human subject.

The present invention also relates to pharmaceutically acceptable form of the drug containing epirubicin or above mentioned epirubicin derivatives of Formula 1, eventually in the form of hydrochloride. In a preferred embodiment, the derivatives of the invention or epirubicin are in the form of hydrochloride.

The present invention concerns new biomedical application of novel derivatives of the invention, and in particular their application to the treatment of hepatitis C virus (HCV) infections.

In this regard, the invention relates to the use of a compound of Formula 1:

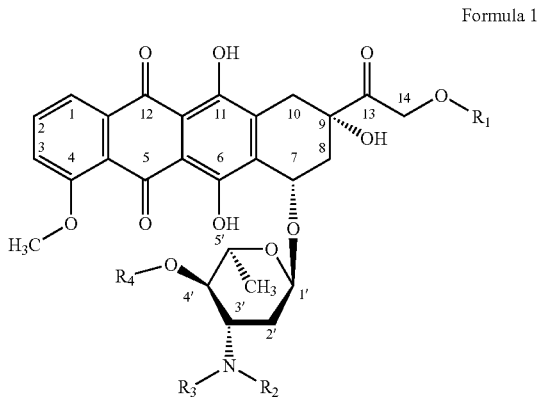

Formula 1 wherein $R_1$, $R_2$, $R_3$, and $R_4$ are the same or different and represent a hydrogen atom; a linear or branched alkyl group comprising from 1 to 5 carbon atoms (such as methyl, ethyl, propyl and isopropyl); a linear or branched alkenyl or alkynyl group with an alkyl chain containing 1 to 5 carbon atoms; an alkyl carbonyl group containing 1 to 5 carbon atoms (such as an acetyl group); or a formamidinyl or dialkylformamidinyl group (with an alkyl chain containing 1 to 5 carbon atoms); and any pharmaceutically acceptable salts thereof; for the manufacture of pharmaceutical composition for treating HCV infection.

According to the present invention, there is provided the use of novel epirubicin derivatives (Formula 1), preferably acetyl derivatives, as active substances for the treatment of HCV virus infections.

This invention relates also to pharmaceutically acceptable forms of the drug containing the mentioned derivatives presented in Formula 1, for the treatment of HCV infection.

In a preferred embodiment, new derivatives of 7-O-(3'-amino-2',3',6'-trideoxy-α,β-L-arabinohexapiranosyl)-adriamycinone (epirubicin) as presented in Formula 1, where $R_1$, $R_2$, $R_3$ and $R_4$ are the same or different: if $R_2$ and $R_3$ is hydrogen then $R_1$ and $R_4$ is hydrogen, if $R_1$, $R_2$, and $R_4$ is hydrogen then $R_3$ is acetyl, if $R_2$ is hydrogen, then $R_1$, $R_3$ and $R_4$ is acetyl, if $R_1$, $R_2$, and $R_4$ is hydrogen then $R_3$ is dimethylformamidinyl, if $R_1$, and $R_4$ is hydrogen then $R_2$ and $R_3$ is methyl group.

Medical application of epirubicin new derivatives rely upon epirubicin derivatives of the invention, preferably presented in Formula 1, wherein $R_1$, $R_2$, $R_3$, and $R_4$ are the same or different: if $R_2$ and $R_3$ is hydrogen then $R_1$ and $R_4$ is hydrogen, if $R_1$, $R_2$, and $R_4$ is hydrogen then $R_3$ is acetyl, if $R_2$ is hydrogen, then $R_1$, $R_3$ and $R_4$ is acetyl, if $R_1$, $R_2$, and $R_4$ is hydrogen then $R_3$ is dimethyl/formamidinyl, if $R_1$, and $R_4$ is hydrogen then $R_2$ and $R_3$ is methyl group.

At present we point first time that new epirubicin derivatives exert potent inhibitory effect on HCV replication at low concentrations and with low toxicity and may be used as effective drugs against HCV infections.

According to the invention, medical application of epirubicin derivatives as anti-HCV agents is characterized as ensuring simultaneously low toxicity against Huh7, PBMC and Vero cells, therapeutic index (TI) better than for epirubicin and lower in vivo acute toxicity.

Pharmaceutically acceptable form of the drug employed against HCV infections, containing known carriers and additions, according to the invention, characterized as containing epirubicin derivatives presented in Formula 1, where $R_1$, $R_2$, $R_3$ and $R_4$ have above mentioned importance, eventually in the form of hydrogen chloride salt.

In investigations as presented below it was pointed out first time, that new epirubicin derivatives as presented in Formula 1 exert inhibitory effect on HCV replication, at low concentrations and may be applied as effective drugs against HCV infections.

The present invention concerns the use of an epirubicin derivative of the present invention or a combination thereof for preparing a medicament for treating or preventing HCV infections. The present invention also concerns a method for treating or preventing HCV infection in a subject comprising administering a therapeutically effective amount of an epirubicin derivative of the present invention or a combination thereof. In a particular embodiment, the derivative of the present invention is used or administered in combination with an other drug, in particular a drug used against HCV infections.

In addition the inventors discovered that Epirubicin hydrochloride, known antitumor drug, is extremely potent anti-HCV agent at very low, nanomolar concentrations. Indeed, they evaluated anti-HCV activity of epirubicin hydrochloride in Huh7 harboring subgenomic HCV replicon and found that $IC_{50}$ of epirubicin is very low i.e. 2-4 nM. The direct comparison of anti-HCV activity of epirubicin hydrochloride found in vitro in cell culture system with the dose used for human antitumour therapy is not possible, since the in vivo study of anti-HCV activity of Epirubicin hydrochloride is hampered by lack of an animal model susceptible to HCV infection, except chimpanzee which is an endangered species. The indirect comparison indicates that anti-HCV $IC_{50}$ of epirubicin hydrochloride is of 2-4 nM, i.e. 7.2-14.5 µg/m$^2$ of body surface (0.035-0.07 mg/m$^2$) as shown by the inventors in vitro in Huh7 cells, whereas the antitumor maximum cumulative dose of Epirubicin hydrochloride in humans is of 900-1000 mg/m$^2$ (Launchburry and Habboubit, *Cancer Treatment Reviews* 1993; 19:197-228). This suggests that anti-HCV activity of Epirubicin hydrochloride demonstrated by the inventors is very low i.e. 14 000-25 000 fold lower than the one use in antitumor therapy.

Therefore, the present invention concerns a method for treating or preventing HCV infection in a subject comprising administering a drug selected in the group consisting of a epirubicin, a derivative thereof according to the invention and a pharmaceutically acceptable salt thereof, at a dose which is at least 10 times, preferably 100 times, even more preferably 1000 times lower than the anti-tumor effective dose. The effective dosage is, e.g., below 100, 50, 10, 1, or 0.1 mg/m$^2$ of body surface. The present invention also concerns the use of a drug selected in the group consisting of a epirubicin, a derivative thereof according to the invention and a pharmaceutically acceptable salt thereof for preparing a medicament for treating or preventing HCV infection, the dose of the drug being lower than 100, 50, 10, 1, or 0.1 mg/m$^2$. The dose can be comprised between 0.001 mg/m$^2$ and 0.1, 1, 10, 50 or 100 mg/m$^2$. In an other embodiment, the dose is comprised between 0.1 or 1 nM and 5, 10, 50 or 100 nM. In a preferred embodiment, the dose is lower than 1 mg/m$^2$. In a particular embodiment, the dose is at least 10 000 times below that used for anti-cancer therapy.

The cumulative dose of the treatment is typically comprised between 0.035-0.07 mg/m$^2$.

Preferably, the pharmaceutically acceptable salt is a hydrochloride salt.

The compounds may be administered by different routes, such as systemic, oral, local or topic routes. Preferred administration route is by injection, typically by intraperitoneal, intravenous or local injection.

The following examples are not intended to limit the scope of the invention in any way.

LEGEND TO THE FIGURES

FIG. 1: Antiviral activity of BN02 on HCV replicon carrying firefly luciferase gene.

Following BNE02 treatment, cells were lysed and firefly luciferase activity was measured using Luminoskan device. Results of anti-HCV activity were expressed as dose-dependant inhibition in reference to the untreated cells taken as 100%.

Figure 2:
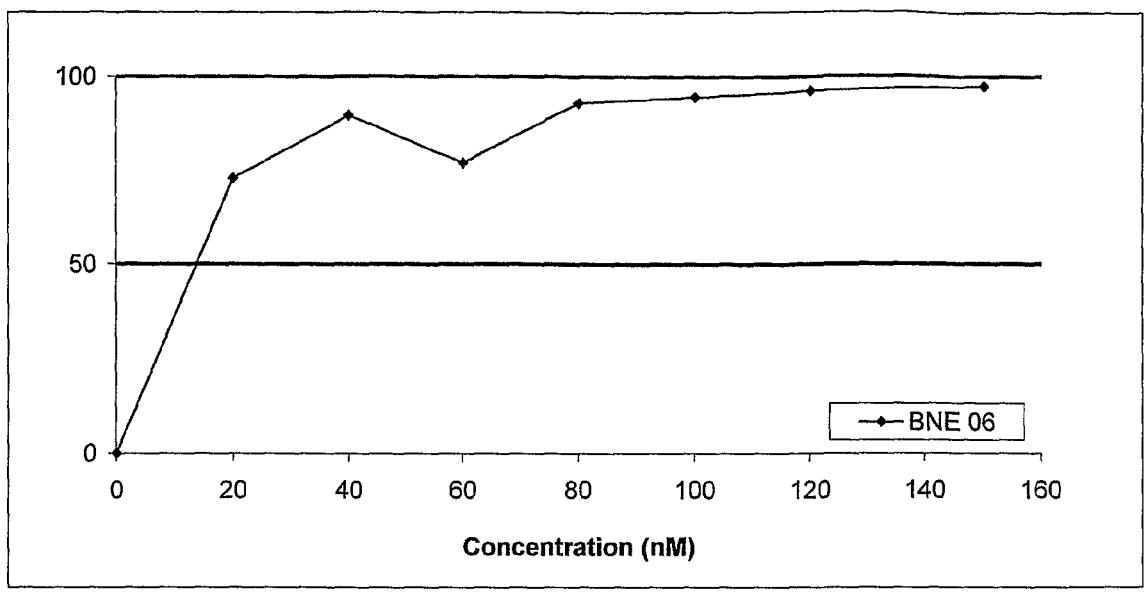

FIG. 2: Antiviral activity of BNE06 on HCV replicon carrying firefly luciferase gene.

Following BN06 treatment, cells were lysed and firefly luciferase activity was measured using Luminoskan device. Results of anti-HCV activity were expressed as dose-dependant inhibition in reference to the untreated cells taken as 100%.

Figure 3:
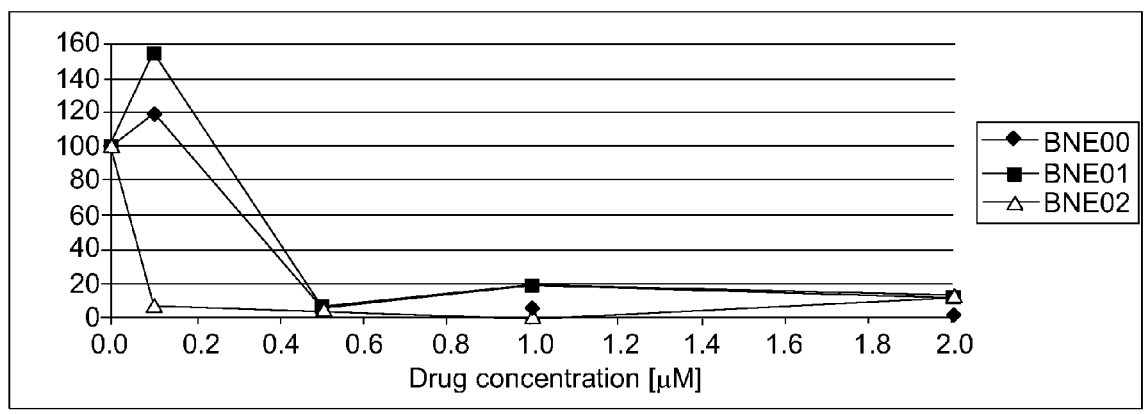

FIG. 3: Inhibition of HCV replication by epirubicin and its derivatives in chronically HCV infected human PBMC cells.

HCV RNA was qualitatively estimated by real-time Reverse Transcriptase Polymerase Chain Reaction using SYBR Green system.

Figure 4:
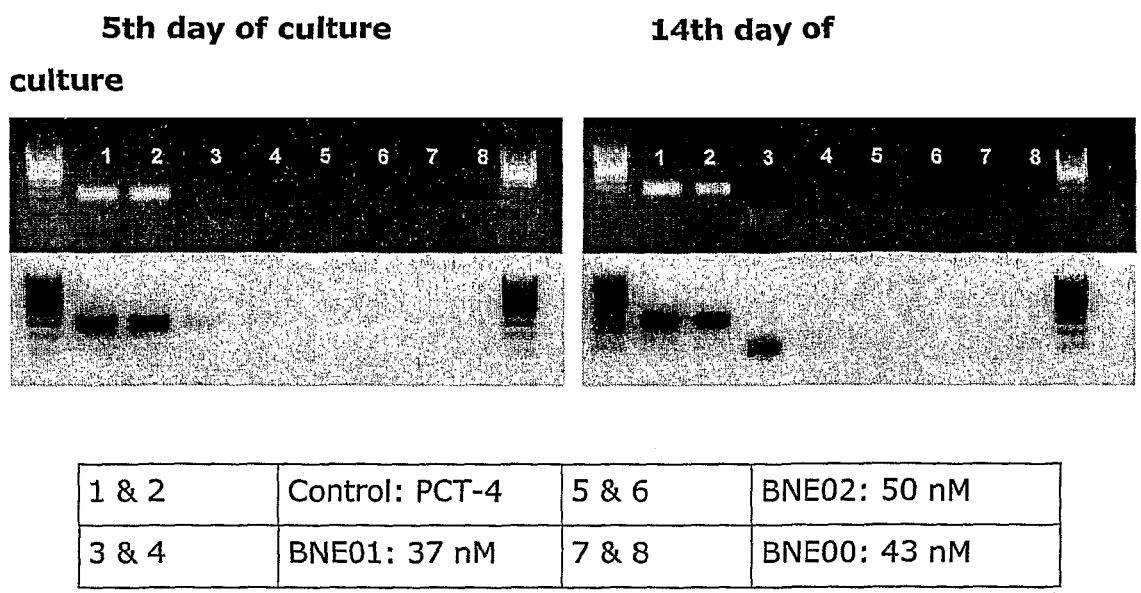

FIG. 4: Effect of epirubicin derivatives on HCV replication in chronically HCV-infected PBMC of PCT-4 patientGel electrophoresis analysis of a Reverse Transcriptase Polymerase Chain Reaction product in untreated cells (controls) and in cells treated with BNE00, BNE01 and BNE02 at concentrations specified above.

Figure 5:
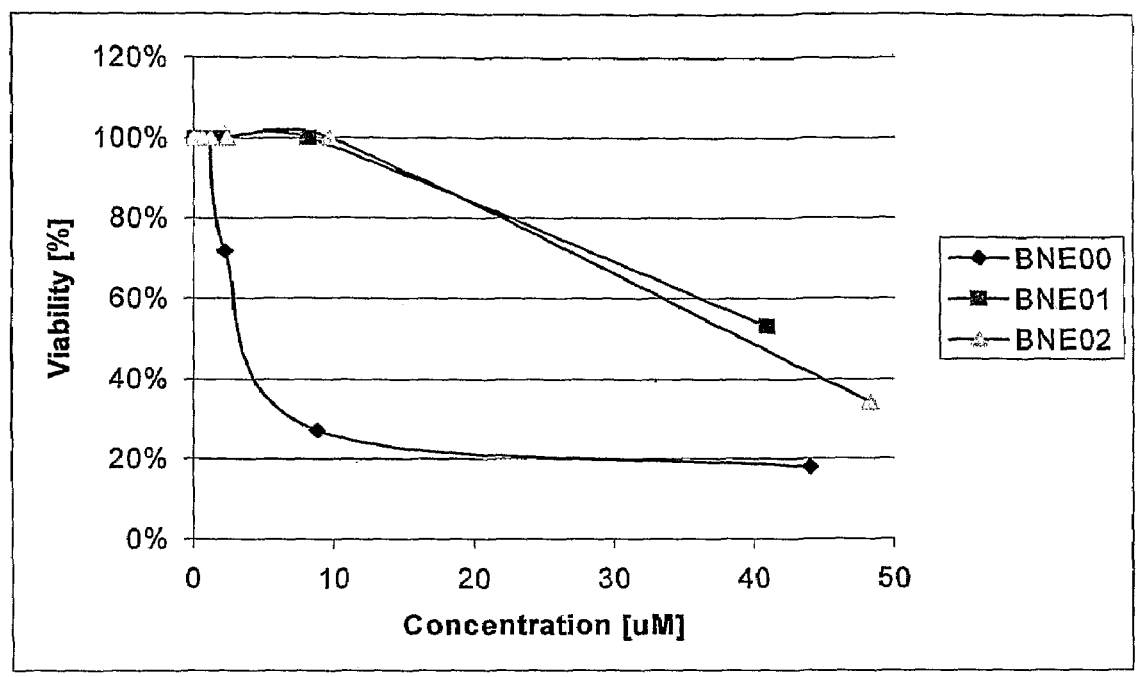

FIG. 5: Cytotoxicity of epirubicin and its derivatives in Vero cells.

EXAMPLE 1

$N_3$,-acetyl-4'-epidoxorubicin (1, BNE01)

4'-epidoxorubicin hydrochloride (58 mg, 0.10 mmol) was dissolved in acetone (6.8 mL) and diisopropylethylamine (18 μL) was added. The solution was cooled to 0° C. in an ice bath and 10 μL (0.11 mmol) of acetic anhydride was added while stirring. The reaction mixture was allowed to warm to room temperature and then stirred for 2 hours. The solution was evaporated and subsequently the residue was dissolved in ca. 13 mL $CHCl_3$. Furthermore the solution was washed with 0.1 M phosphate buffer pH 7.0 (3 times), and water (2 times). The organic layer was dried over anhydrous sodium sulphate and evaporated under vacuum. The residue was chromatographed (column of silica gel; $CHCl_3$ to $CHCl_3$:MeOH 1:1); m. p. 180° C.; MS (ES+) 586.14; NMR ($CDCl_3$) δ 1.36 (d, 3, 5'-$CHCl_3$), 2.01 (s, 3, 3'-N—$COCH_3$), 2.06 (m, 2, 2'-$H_2$), 2.19 (d, 1, 8A-H), 2.41 (d, 1, 8B-H), 3.02-3.12 (m, 3, 3'-H and 4'-H/4'-OH), 3.28 (d, 1, 10A-H), 3.32 (d, 1, 10B-H), 3.78-3.81 (m, 1, 5'-H), 4.09 (s, 3, 4-$OCH_3$), 4.80 (dd, 3, 14-$H_2$/14-OH), 5.30 (br s, 1, 9-OH), 5.43 (d, 1, 1'-H), 5.51 (d, 1, 7-H), 7.41 (d, 1, 3-H), 7.80 (t, 1, 2-H), 8.05 (d, 1, 1-H), 13.26 (s, 1, 11-OH), 14.02 (s, 1, 6-OH).

EXAMPLE 2

$N_3$, $O_4$, $O_{14}$-triacetyl-4'-epidoxorubicin (2, BNE02)

4'-epidoxorubicin hydrochloride (100 mg, 0.17 mmol) was dissolved in dry chloroform (10 mL) and 20 mg 4-dimethylaminopyridine was added. The solution was cooled to 0° C. in an ice bath and 400 μL (4.24 mmol) of acetic anhydride was added while stirring. The reaction mixture was allowed to warm to room temperature and then stirred. The progress of the reaction was checked by TLC ($CHCl_3$:MeOH 9:1). Then the solution was washed with 0.1 M phosphate buffer pH 7.0 (3 times), and water (2 times). The organic layer was dried over anhydrous sodium sulphate and evaporated in vacuo. The residue was chromatographed (column of silica gel; $CHCl_3$ to $CHCl_3$:MeOH 1:1); m. p. 178° C.; MS (ES+) 670.25. NMR (DMSO-$d_6$) δ 1.09 (d, 3, 5'-$CH_3$), 1.69 (s, 3, 14-O—$COCH_3$), 1.97 (s, 3, 4'-O—$COCH_3$), 2.08-2.12 (m, 5, 3'-N—$COCH_3$, 8$H_2$), 2.94/3.08 (d/d, 1/1, 2'-$H_2$), 4.05 (s, 3, 4-$OCH_3$), 4.10-4.13 (m, 1, 5'-H), 4.43 (t, 1, 1'-H), 4.96-4.97 (m, 1, 7-H), 5.22 (d, 2, 14-$H_2$), 5.79 (s, 1, 9-OH), 7.66 (t, 1, 2-H), 7.72 (d, 1, 3-H), 7.92 (d, 1, 1-H), 13.28 (s, 1, 11-OH), 14.01 (s, 1, 6-OH).

EXAMPLE 3

3'-N,N-Dimethyl-4'-epidoxorubicin (3, BNE06)

To a stirred solution of 4'-epidoxorubicin hydrochloride (100 mg, 0.17 mmol) in 630 μL $H_2O$, 1.3 mL of acetonitrile was added and the mixture was warmed to 30° C. Then 130 μL of 37% aqueous solution of formaldehyde (1.31 mmol) was added and the solution was stirred for 20 minutes in 23-25° C. Next $NaCNBH_3$ (23 mg, 0.37 mmol in 1.3 mL of acetonitrile) was added drop wise over 15 minutes. After the addition stirring was continued at 24° C. for 20 minutes. Then the reaction mixture was diluted with water (4 mL) and extracted with $CHCl_3$ (2×4 mL). The chloroform extracts were combined, dried over anhydrous sodium sulphate and evaporated in vacuo. The residue was chromatographed (silica gel PLC plates) in $CHCl_3$: MeOH:$H_2O$ 40:10:1); m. p. 220° C.; MS (ES+) 572.28, (ES−) 570.22. NMR (DMSO-$d_6$) δ 1.20 (d, 3, 5'-$CH_3$), 1.56 (dt, 1, 2'-H), 1,72 (dd, 1, 2'-H), 2.17 (br s, 8, 3'-N($CH_3$)$_3$, 8-$H_2$) 2.91-3.08 (m, 4, 10-H, 4'-OH, 4'-H, 3'-H), 3.80-3.85 (m, 1, 5'-H), 3.99 (s, 3, 4-$OCH_3$), 4.55 (br s, 2, 14-$H_2$), 4.85 (br s, 1, 14-OH), 4.97 (t, 1, 1'-H), 5.32 (d, 1, 7-H), 5.45 (s, 1, 9-OH), 7.62 (d, 1, 3-H), 7.89 (t, 1, 2-H), 7.94 (d, 1, 1-H), 13.24 (br s, 1, 11-OH), 14.30 (br s, 1, 6-OH).

EXAMPLE 4

3'-N—(N'',N''-Dimethylformamidinyl)-4'-epidoxorubicin (4, BNE04)

To a solution of 4'-epidoxorubicin hydrochloride (150 mg, 0.26 mmol, 1 equiv) in dry methanol (7.5 mL) N,N-dimethylformamide dimethyl acetal (182 μL, 1.30 mmol, 5 equiv) was added dropwise under Ar. The reaction mixture was stirred for 4 hours, and then solvent was removed under reduced pressure. The residue was chromatographed (column of silica gel; $CHCl_3$ to $CHCl_3$:MeOH 9:1); m. p. 206° C.; MS (ES+) 599.13, (ES−) 597.24; NMR (DMSO-$d_6$) δ 1.24 (d, 3, 5'-$CH_3$), 1.99 (d, 2, 8$H_2$), 2.19 (m, 2, 2'-$H_2$), 3.01-3.11 (m and m, 11, 10-$H_2$, 4'-OH, 4'-H, 3'-H, N'''-$Me_2$), 3.93 (m, 1, 5'-H), 4.00 (s, 3, 4-$OCH_3$), 4.57 (d, 2, 14-$H_2$), 4.87 (t, 1, 14-OH), 4.99 (t, 1, 1'-H), 5.29 (t, 1, 7-H), 5.48 (s, 1, 9-OH), 7.68 (t, 1, 2-H), 7.94 (d, 2, 1-H and 3-H), 8.08 (s, 1, 3'-NC''-H), 13.26 (s, 1, 11-OH), 14.04 (s, 1, 6-OH).

Antiviral Activity and Cytotoxicity Testing.

The antiviral (anti-HCV) activity of epirubicin and its derivatives was tested in vitro in cell culture model using the HCV subgenomic replicon stably transfected into Huh7 ced line (clone BM4.5) (Gao et al., J. Virol. 2001) and/or in Huh7 cells replicating selectable subgenomic HCV replicon carrying firefly luciferase gene (Vrolijk et al. J. Virol. Method. 2003).

The BM4.5 Huh7 cells were grown in cell culture medium in presence of varying concentrations of epirubicin hydrochloride (BNE00) or epirubicin derivatives. The media and drug were changed everyday for 5 days. After 5 days of treatment cells were lysed and total RNA extracted as described (Gao et al., J. Virol. 2001). The isolated RNA was then assayed for presence of HCV replication by Northern Blot analysis, using a HCV probe targeting the NS5B region of HCV. In addition, the hybridization with the β-actin radiolabelled probe allowed the normalization of the results i.e. to assess the impact of drug on housekeeping gene expression. The cell lines were treated everyday with different epirubicin hydrochloride (BNE00) or epirubicin derivatives concentrations for 5 days and at the end of treatment, the RNA from the treated cells were isolated. The total RNA was then probed with a HCV specific probe using Northern blot analysis to detect the HCV RNA. The resulting blot was then exposed to phosphorimager densitometry and the viral replication quantified.

For Huh7 cells replicating selectable subgenomic HCV replicon carrying firefly luciferase gene cells were treated with epirubicin hydrochloride (BNE00) or epirubicin derivatives as described above for BM4,5 cells. Following the treatment, cells were lysed and firefly luciferase activity was measured using Luminoskan device (Thermolabsystem) as described (Vrolijk et al. J. Virol. Methods. 2003).

Results of anti-HCV activity were expressed as dose-dependant inhibition in reference to the untreated cells taken as 100%. The obtained data indicate that epirubicin hydrochloride and epirubicin derivatives effectively inhibit in vitro HCV replication in HCV subgenomic replicon with $IC_{50}$ ranging from 0.002 to 0.5 μM as summarized in Table 1 and illustrated in FIGS. 1-2 for BNE02 and BNE06, respectively.

In addition, the inhibition of HCV replication by epirubicin hydrochloride (BNE00), N3'-acetylepirubicin (BNE01), and $N_{3'},O_{4'},O_{14}$-triacetylepirubicin (BNE02) were analyzed in chronically HCV-infected human peripheral blood monocyte cells (PBMC) cultures which was performed as follows. PBMC were isolated from HCV-infected patients blood by Ficoll Pague centrifugation placed on Petri dishes and cultured in 10% FCS, RPMI medium containing PHA (3 μg/ml) according to Laskus et al. (J Infect Dis. 2000) and enriched with known concentrations of BNE00, BNE01, BNE02 in standard conditions (37° C., 5% $CO_2$). On day 5 and 14 of the culture the cells were collected and after extraction, HCV RNA was qualitatively estimated by real-time Reverse Transcriptase Polymerase Chain Reaction using SYBR Green system (FIG. 3). Semiquantitative estimation of HCV RNA was also performed by Reverse Transcriptase Polymerase Chain Reaction, and visualized after electrophoresis through a 1% agarose gel, using ethidium bromide staining (FIG. 4).

Results of analysis of dependency from drug concentrations indicate, that epirubicin hydrochloride (BNE00) and epirubicin derivatives effectively inhibit in vitro HCV replication in chronically HCV infected human PBMC with $IC_{50}$ ranging from 0.10 to 0.36 μM (Table 2).

In addition to PBMC, the cytotoxicity estimation of epirubicin (BNE00), N3'-acetylepirubicin (BNE01), and N3',O4', O14-triacetylepirubicin (BNE02) was also performed in Vero cells. Briefly Vero cells were seeded in 96-well flat bottom plates (4000 cells per well) in the medium enriched with increasing concentrations of tested compounds and cultured in standard conditions. After 7-days and 14-days incubation the cell viability was measured with tetrazolium based (MTT) colorimetric assay. Cytotoxicity ($CC_{50}$) of epirubicin derivatives in Vero cells was in a range of 33-49 μM (FIG. 5).

In Table 1, it was also pointed that $IC_{50}$ of epirubicin hydrochloride (BNE00) and epirubicin derivatives (BNE01, BNE02) with regards to the anti-HCV activity, measured in HCV replicon system, was found to be low since it was in a range 0.002 to 0.5 μM, while its $CC_{50}$ in Huh7 cells was in the range 0.003-5 μM, profitably in the case of $N_3',O_4',O_{14}$-triacetylepirubicin (BNE02), where therapeutic index is 10. It is to point out that the Huh7 harbouring HCV replicon are extremely sensitive to cytotoxicity of drugs. Accordingly, our analysis of BNE02 in PBMCs showed lower toxicity ($CC_{50}$ 49 μM) and better therapeutic index (>490).

The in vivo determination of acute toxicity of drugs was performed in mice according to "OECD Guidelines for Testing of Chemicals" (Guideline No 401). The study was performed in BALB/C mice and the test substance was administrated intraperitoneally in dose of 1; 5 and 10 mg/kg b.w. Ten males and 10 females were used for each dose. A control group receiving only solvent was run concurrently. Importantly, compound 2 (BNE02) exerts very low in vivo acute toxicity ($LD_{50}$=1355.08 mg/kg b.w. of mice) as compared with epirubicin hydrochloride (BNE00) ($LD_{50}$=26.17 mg/kg b.w. of mice), tested in parallel, indicated a 52-fold lower toxicity of this derivative.

In this study, we show for the first time that epirubicin derivatives are capable to exert anti-HCV effects at low concentrations and good therapeutic index and should be regarded as potent drugs against HCV infections with very low toxicity in vitro and in vivo.

TABLE 1

Anti-HCV activity in HCV replicon system and cytotoxicity of epirubicin derivatives in Huh7 cells.

| Compound | Cytotoxic activity[1] in Huh7 Cells, $CC_{50}$ (μM) | Anti-HCV activity[2] in HCV replicon system $IC_{50}$ (μM) | Therapeutic Index in HCV replicon system $CC_{50}/IC_{50}$ |
|---|---|---|---|
| Epirubicin hydrochloride (BNE00) | 0.003 | 0.002 | 1.5 |
| 2. $N_3',O_4',O_{14}$-triacetyl-epirubicin (BNE02) | 5 | 0.5 | 10.0 |
| 3. 3'-N,N-Dimethyl-4'-epidoxorubicin (BNE06) | 0.06 | 0.018 | 3.0 |

Anti-HCV activity and cytotoxicity were evaluated in Huh7 cells replicating selectable subgenomic HCV replicon carrying firefly luciferase gene as described (Vrolijk et al. J. Virol. Methods. 2003).
[1]Cytotoxic activity ($CC_{50}$) - 50% cytotoxic concentration
[2]Antiviral activity ($IC_{50}$) - concentration required to inhibit viral replication by 50%

In Table 2 are presented data of cytotoxicity ($CC_{50}$ and $CC_{90}$), anti-HCV activity ($IC_{50}$ and $IC_{90}$) and of therapeutic index ($TI_{50}$ and $TI_{90}$) in human PBMC from chronic HCV-infected patients.

TABLE 2

Anti-HCV activity and cytotoxicity of epirubicin derivatives in chronically HCV-infected human PBMC cells

| Compound | Cytotoxic[1] activity in PBMC $CC_{50}$ (μM) | | Anti-HCV[2] activity in PBMC $IC_{50}$ (μM) | | Therapeutic Index in PBMC | |
|---|---|---|---|---|---|---|
| | $CC_{50}$ | $CC_{90}$ | $IC_{50}$ | $IC_{90}$ | $CC_{50}/IC_{50}$ | $CC_{90}/IC_{90}$ |
| Epirubicin hydrochloride (BNE00) | 1.8 | 2.4 | 0.32 | 0.46 | 5.62 | 5.21 |

TABLE 2-continued

Anti-HCV activity and cytotoxicity of epirubicin derivatives in chronically HCV-infected human PBMC cells

| | Cytotoxic[1] activity in PBMC | | Anti-HCV[2] activity in PBMC | | Therapeutic Index in PBMC | |
|---|---|---|---|---|---|---|
| | $CC_{50}$ (μM) | | $IC_{50}$ (μM) | | $TI_{50}$ | $TI_{90}$ |
| Compound | $CC_{50}$ | $CC_{90}$ | $IC_{50}$ | $IC_{90}$ | $CC_{50}/IC_{50}$ | $CC_{90}/IC_{90}$ |
| $N_3$'-acetylepirubicin (BNE01) | 33.0 | 91.0 | 0.36 | 0.47 | 91.7 | 194.0 |
| $N_3$',$O_4$',$O_{14}$-triacetyl-epirubicin (BNE02) | 49.0 | 120.0 | <0.10 | 0.50 | >490.0 | 240.0 |

[1]Cytotoxic activity ($CC_{50}$ or $CC_{90}$) - 50% or 90% cytotoxic concentration
[2]Antiviral activity ($IC_{50}$ or $IC_{90}$) - concentration required to inhibit viral replication by 50% or 90%

The invention claimed is:

1. A compound having Formula 1:

(1)

[Chemical structure of Formula 1]

wherein $R_1$, $R_2$, and $R_3$ are the same or different and represent a hydrogen atom; a linear or branched alkyl group comprising from 1 to 5 carbon atoms; a linear or branched alkenyl or alkynyl group with an alkyl chain containing 1 to 5 carbon atoms; an alkyl carbonyl group containing 1 to 5 carbon atoms; or a formamidinyl or dialkylformamidinyl group with an alkyl chain containing 1 to 5 carbon atoms, and $R_4$ represents a linear or branched alkyl group comprising from 1 to 5 carbon atoms; a linear or branched alkenyl or alkynyl group with an alkyl chain containing 1 to 5 carbon atoms; an alkyl carbonyl group containing 1 to 5 carbon atoms; or a formamidinyl or dialkylformamidinyl group with an alkyl chain containing 1 to 5 carbon atoms, or a pharmaceutically acceptable salt thereof.

2. The compound of claim 1, wherein at least one of $R_1$, $R_2$, $R_3$, and $R_4$ is a hydrogen atom.

3. The compound of claim 1, wherein at least one of $R_1$, $R_2$, $R_3$, and $R_4$ is an alkyl carbonyl group.

4. The compound of claim 1, wherein $R_3$ is an acetyl group.

5. The compound of claim 1, wherein at least one of $R_1$, $R_2$, $R_3$, and $R_4$ is an alkyl group.

6. The compound of claim 1, wherein at least one of $R_1$, $R_2$, $R_3$, and $R_4$ is a dialkylformamidinyl group.

7. The compound of claim 1, wherein the pharmaceutically acceptable salt is a hydrochloride salt.

8. A pharmaceutical composition comprising a compound according to claim 1 and a pharmaceutically acceptable carrier.

9. A compound according to claim 1 as a medicament.

10. A method for treating or preventing HCV infections, the method comprising:
administering to a mammalian subject an effective amount of a compound having formula 1:

(1)

[Chemical structure of Formula 1]

wherein $R_1$, $R_2$, $R_3$, and $R_4$ are the same or different and represent a hydrogen atom; a linear or branched alkyl group comprising from 1 to 5 carbon atoms; a linear or branched alkenyl or alkynyl group with an alkyl chain containing 1 to 5 carbon atoms ; an alkyl carbonyl group containing 1 to 5 carbon atoms; or a formamidinyl or dialkylformamidinyl group; or a pharmaceutically acceptable salt thereof.

11. The method of claim 10 wherein:

$R_1$, $R_2$, and $R_4$ are hydrogen and $R_3$ is acetyl, or $R_2$ is hydrogen and $R_1$, $R_3$ and $R_4$ are acetyl, or $R_1$, $R_2$, and $R_4$ are hydrogen and $R_3$ is dimethylformamidinyl or formamidinyl, or $R_1$ and $R_4$ are hydrogen and $R_2$ and $R_3$ are meethyl group, or, $R_1$ and $R_2$ represent an hydrogen atom and $R_3$ and $R_4$ represent acetyl groups.

12. The method of claim 10 wherein the mammalian subject is administered a dose below 100 mg/m².

13. The method of claim 10 whererin the mammalian subject is administered a dose below 50 mg/m².

14. The method of claim 10 whererin the mammalian subject is administered a dose below 10 mg/m².

15. The method of claim 10 whererin the mammalian subject is administered a dose below 0.1 mg/m².

16. The compound of claim 1, wherein at least one of $R_1$, $R_2$, $R_3$, and $R_4$ is an acetyle group.

17. The compound of claim 1, wherein at least one of $R_1$, $R_2$, $R_3$, and $R_4$ is a methyl group.

18. The compound of claim 1, wherein at least one of $R_1$, $R_2$, $R_3$, and $R_4$ is a dimethylformamidinyl group.

19. A compound having Formula 1:

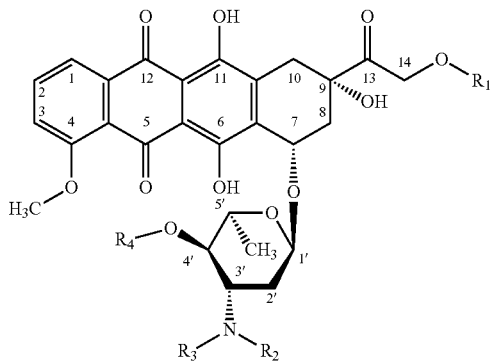

wherein:
- $R_1$, $R_2$, and $R_4$ are hydrogen and $R_3$ is acetyl, or
- $R_2$ is hydrogen and $R_1$, $R_3$ and $R_4$ are acetyl, or
- $R_1$, $R_2$, and $R_4$ are hydrogen and $R_3$ is dimethylformamidinyl or formamidinyl, or
- $R_1$ and $R_4$ are hydrogen and $R_2$ and $R_3$ are methyl group, or,
- $R_1$ and $R_2$ represent an hydrogen atom and $R_3$ and $R_4$ represent acetyl groups, or a pharmaceutically acceptable salt thereof.

20. A method for treating or preventing HCV infections, the method comprising:
administering to a mammalian subject and effective amount of a compound having formula 1:

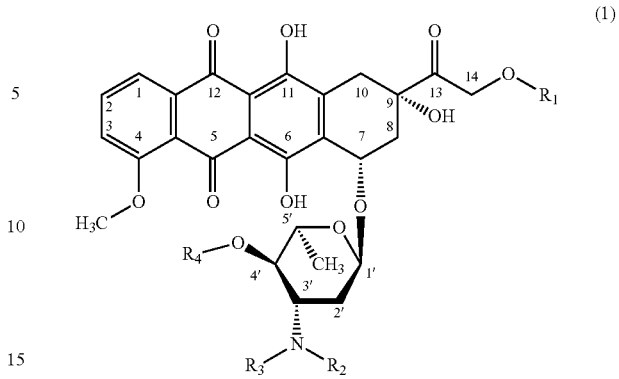

wherein:
- $R_1$, $R_2$, and $R_4$ are hydrogen and $R_3$ is acetyl, or
- $R_2$ is hydrogen and $R_1$, $R_3$ and $R_4$ are acetyl, or
- $R_1$, $R_2$, and $R_4$ are hydrogen and $R_3$ is dimethylformamidinyl or formamidinyl, or
- $R_1$ and $R_4$ are hydrogen and $R_2$ and $R_3$ are methyl group, or,
- $R_1$ and $R_2$ represent an hydrogen atom and $R_3$ and $R_4$ represent acetyl groups, or a pharmaceutically acceptable salt thereof.

21. The compound of claim 1, wherein at least one of $R_1$, $R_2$, $R_3$, and $R_4$ is a dimethylformamidinyl group.

* * * * *